(12) United States Patent
Oka

(10) Patent No.: US 10,709,320 B2
(45) Date of Patent: Jul. 14, 2020

(54) ILLUMINATION OPTICAL SYSTEM AND IMAGE-ACQUISITION APPARATUS

(71) Applicant: OLYMPUS CORPORATION, Hachioji-shi, Tokyo (JP)

(72) Inventor: Tetsuhiro Oka, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 16/159,092

(22) Filed: Oct. 12, 2018

(65) Prior Publication Data

US 2019/0046023 A1 Feb. 14, 2019

Related U.S. Application Data

(63) Continuation of application No. PCT/JP2016/061960, filed on Apr. 14, 2016.

(51) Int. Cl.
*A61B 1/05* (2006.01)
*A61B 1/06* (2006.01)
(Continued)

(52) U.S. Cl.
CPC ........ *A61B 1/0684* (2013.01); *A61B 1/00096* (2013.01); *A61B 1/05* (2013.01);
(Continued)

(58) Field of Classification Search
CPC ..... A61B 1/00009; A61B 1/05; A61B 1/0676; A61B 1/0684; G02B 23/2423
See application file for complete search history.

(56) References Cited

U.S. PATENT DOCUMENTS

| 4,684,224 A | 8/1987 | Yamashita et al. |
| 6,334,688 B1 | 1/2002 | Niwa |

(Continued)

FOREIGN PATENT DOCUMENTS

| EP | 2469322 A1 | 6/2012 |
| EP | 2570072 A1 | 3/2013 |

(Continued)

OTHER PUBLICATIONS

International Search Report (ISR) dated Jun. 21, 2016 issued in International Application No. PCT/JP2016/061960.

(Continued)

*Primary Examiner* — Obafemi O Sosanya
(74) *Attorney, Agent, or Firm* — Holtz, Holtz & Volek PC

(57) ABSTRACT

An illumination optical system according to the present invention is provided with: an illumination-light guiding portion configured to guide illumination light emitted from a light source portion; and an illumination-light deflecting portion configured to emit the illumination light guided thereto by the illumination-light guiding portion after deflecting the illumination light by means of reflection, wherein, in one cross-section along a direction in which the illumination light travels, the illumination-light guiding portion has a pair of total reflection surfaces in which the distance therebetween gradually increases in a forward traveling direction of the illumination light, and the illumination-light deflecting portion is provided with an emission surface from which the illumination light guided by the illumination-light guiding portion is emitted, and a reflection surface that has a convex shape facing the emission surface and that reflects the illumination light guided by the illumination-light guiding portion toward the emission surface.

12 Claims, 21 Drawing Sheets

(51) Int. Cl.
*G02B 23/24* (2006.01)
*A61B 1/07* (2006.01)
*A61B 1/00* (2006.01)

(52) U.S. Cl.
CPC .......... *A61B 1/0615* (2013.01); *A61B 1/0676* (2013.01); *A61B 1/07* (2013.01); *G02B 23/2423* (2013.01); *A61B 1/00009* (2013.01)

(56) References Cited

U.S. PATENT DOCUMENTS

| | | |
|---|---|---|
| 2010/0312057 A1 | 12/2010 | Konno |
| 2012/0134159 A1 | 5/2012 | Kamo et al. |
| 2013/0070072 A1 | 3/2013 | Honda |
| 2014/0347878 A1* | 11/2014 | Honda ............... G02B 23/2461 362/574 |
| 2016/0103312 A1 | 4/2016 | Furuta |

FOREIGN PATENT DOCUMENTS

| | | |
|---|---|---|
| EP | 2815691 A1 | 12/2014 |
| EP | 3020321 A1 | 5/2016 |
| JP | 59087403 A | 5/1984 |
| JP | H07124100 A | 5/1995 |
| JP | H09285440 A | 11/1997 |
| JP | 2000207916 A | 7/2000 |
| JP | 2002078672 A | 3/2002 |
| JP | 2010021105 A | 1/2010 |
| JP | 2010102154 A | 5/2010 |
| JP | 2014132918 A | 7/2014 |
| JP | 2015016021 A | 1/2015 |
| JP | 2015204136 A | 11/2015 |
| WO | 2010055800 A1 | 5/2010 |
| WO | 2011058912 A1 | 5/2011 |
| WO | 2012132598 A1 | 10/2012 |
| WO | 2014073426 A1 | 5/2014 |

OTHER PUBLICATIONS

Written Opinion dated Jun. 21, 2016 issued in International Application No. PCT/JP2016/061960.

* cited by examiner

ILLUMINATION OPTICAL SYSTEM AND IMAGE-ACQUISITION APPARATUS

CROSS-REFERENCE TO RELATED APPLICATIONS

This is a continuation of International Application PCT/JP2016/061960, with an international filing date of Apr. 14, 2016, which is hereby incorporated by reference herein in its entirety.

TECHNICAL FIELD

The present invention relates to an illumination optical system and an image-acquisition apparatus.

BACKGROUND ART

There is a known endoscope that has an angle of view that is equal to or greater than 180°, and with which it is possible to simultaneously observe front, lateral, and rear viewing fields (for example, see Patent Literature 1). For example, in the case in which an endoscope having an angle of view that is equal to or greater than 180° is used in the colon, in which numerous folds are present, with the endoscope of Patent Literature 1, it is possible to observe the back side of a fold without greatly changing the direction in which the distal end of the endoscope points, and thus, manipulations by a user are facilitated, and it is possible to more reliably find a lesion. An illumination apparatus of this endoscope is capable of uniformly illuminating large lateral and front areas by diffusing, by means of a diffusion layer, illumination light guided by a light guide.

CITATION LIST

Patent Literature

{PTL 1} Japanese Unexamined Patent Application, Publication No. 2015-16021

Summary of Invention

An aspect of the present invention is an illumination optical system comprising: an illumination-light guiding portion configured to guide illumination light emitted from a light source portion; and an illumination-light deflecting portion configured to emit the illumination light guided thereto by the illumination-light guiding portion after deflecting the illumination light by means of reflection; wherein, in one cross-section along a direction in which the illumination light travels, the illumination-light guiding portion has a pair of total reflection surfaces in which the distance therebetween gradually increases in a forward traveling direction of the illumination light, and the illumination-light deflecting portion is provided with an emission surface from which the illumination light guided by the illumination-light guiding portion is emitted, and a reflection surface that has a convex shape facing the emission surface and that reflects the illumination light guided by the illumination-light guiding portion toward the emission surface.

Another aspect of the present invention is an image-acquisition apparatus comprising: an image-capturing optical system that has an optical axis and that captures an image of an area surrounding the optical axis; and a single or a plurality of the aforementioned illumination optical systems, disposed so as to surround the optical axis.

DESCRIPTION OF EMBODIMENT

An illumination optical system 15 and an image-acquisition apparatus 1 according to an embodiment of the present invention will be described below with reference to the drawings.

Figure 1:
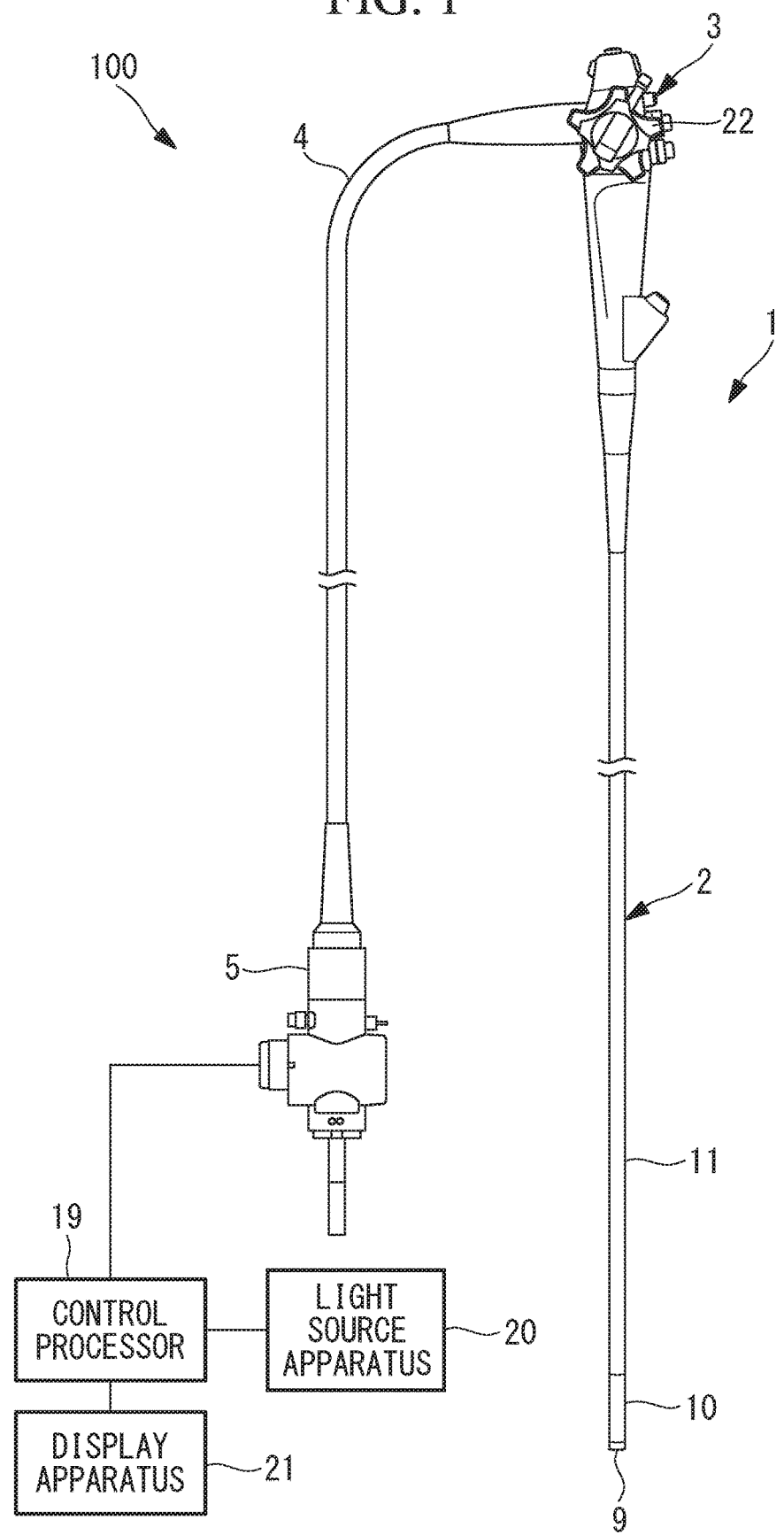
FIG. 1 is an overall configuration diagram showing an endoscope as an example of an image-acquisition apparatus according to an embodiment of the present invention.

As shown in FIG. 1, the image-acquisition apparatus 1 according to this embodiment is an endoscope provided with: a long, thin inserted portion 2 that is inserted into a body cavity or the like; a manipulating portion 3 that is provided at a base end of the inserted portion 2; a universal cord 4 that extends from the manipulating portion 3; and a connector 5 that is provided at a terminal end of the universal cord 4.

Figure 2:
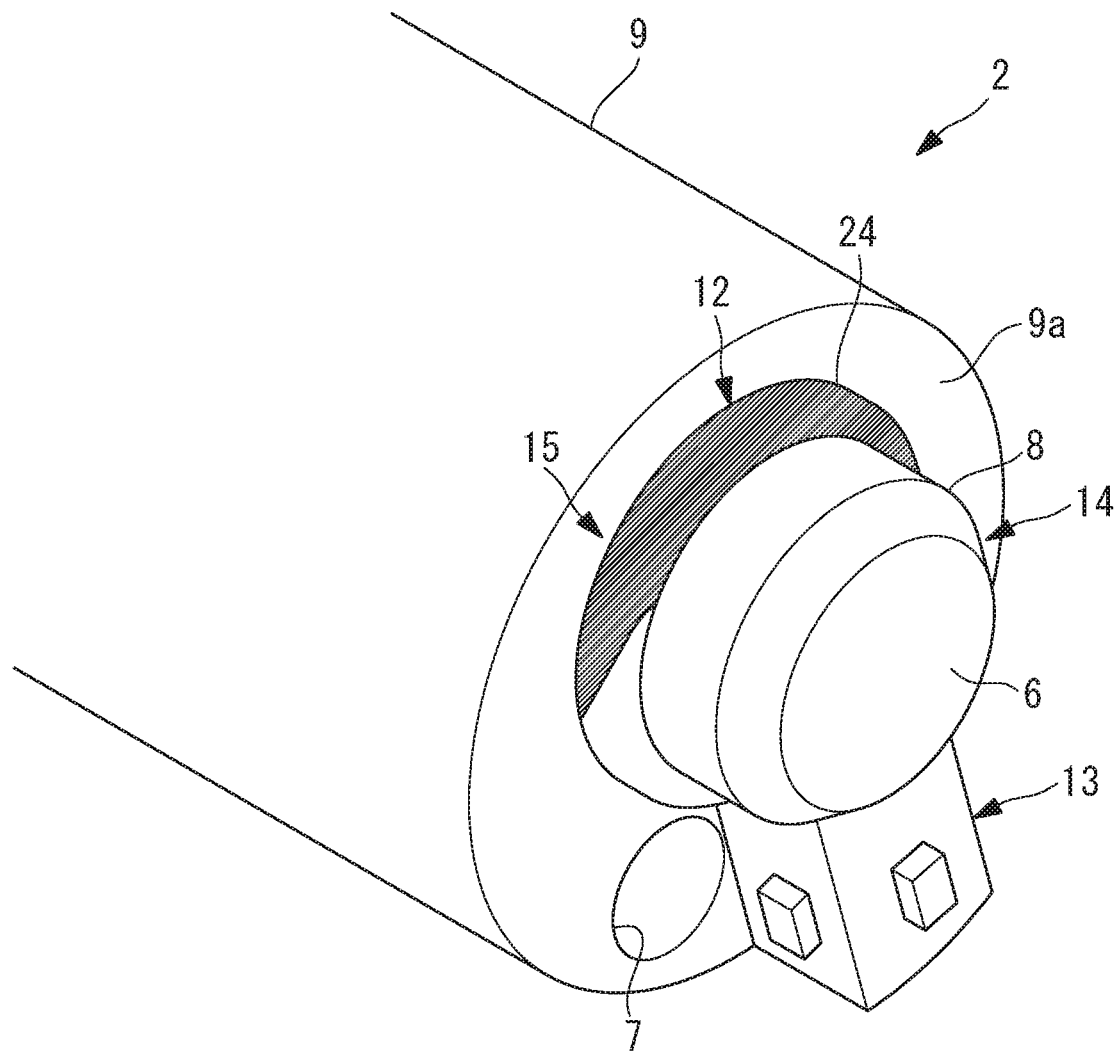
FIG. 2 is a perspective view showing, in an enlargement, a portion of a distal-end portion of the image-acquisition apparatus in FIG. 1.
Figure 3:
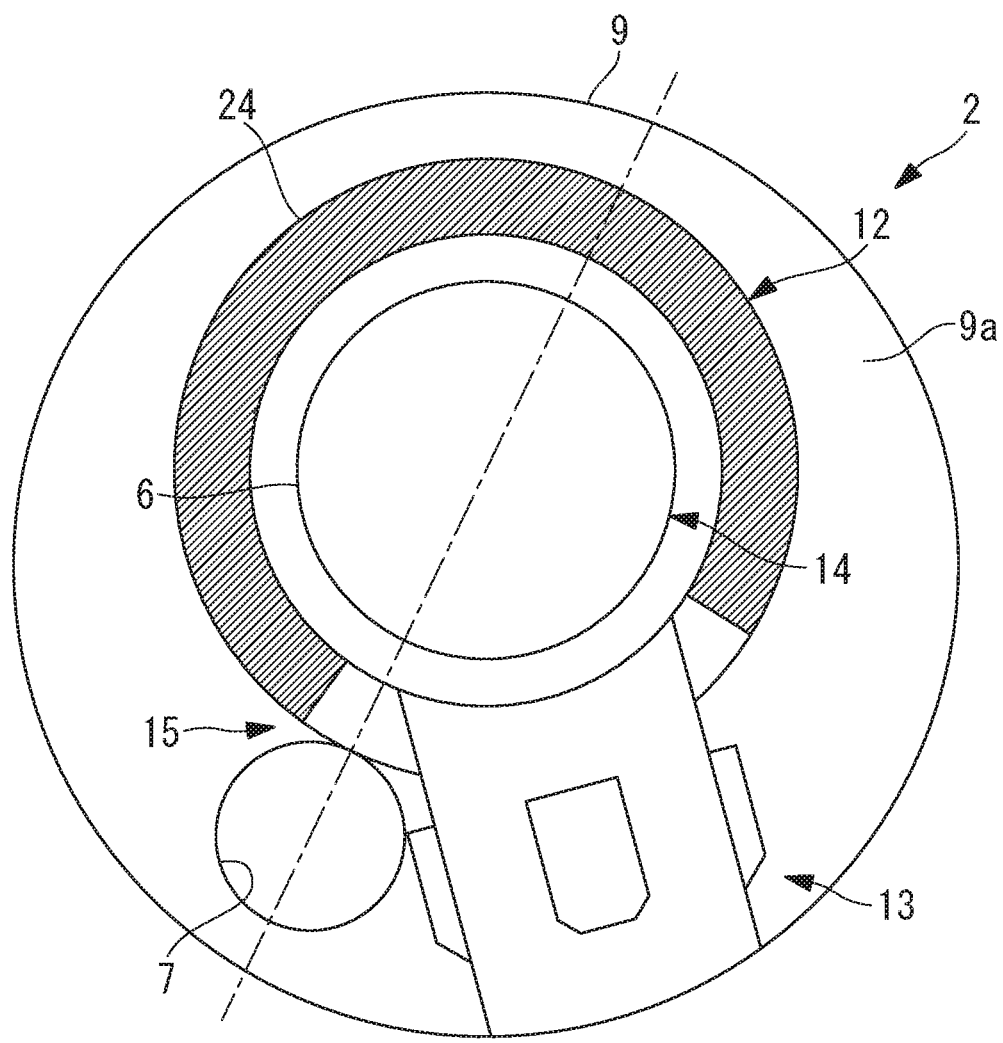
FIG. 3 is a front view showing the distal-end portion of the image-acquisition apparatus in FIG. 2.
Figure 4:
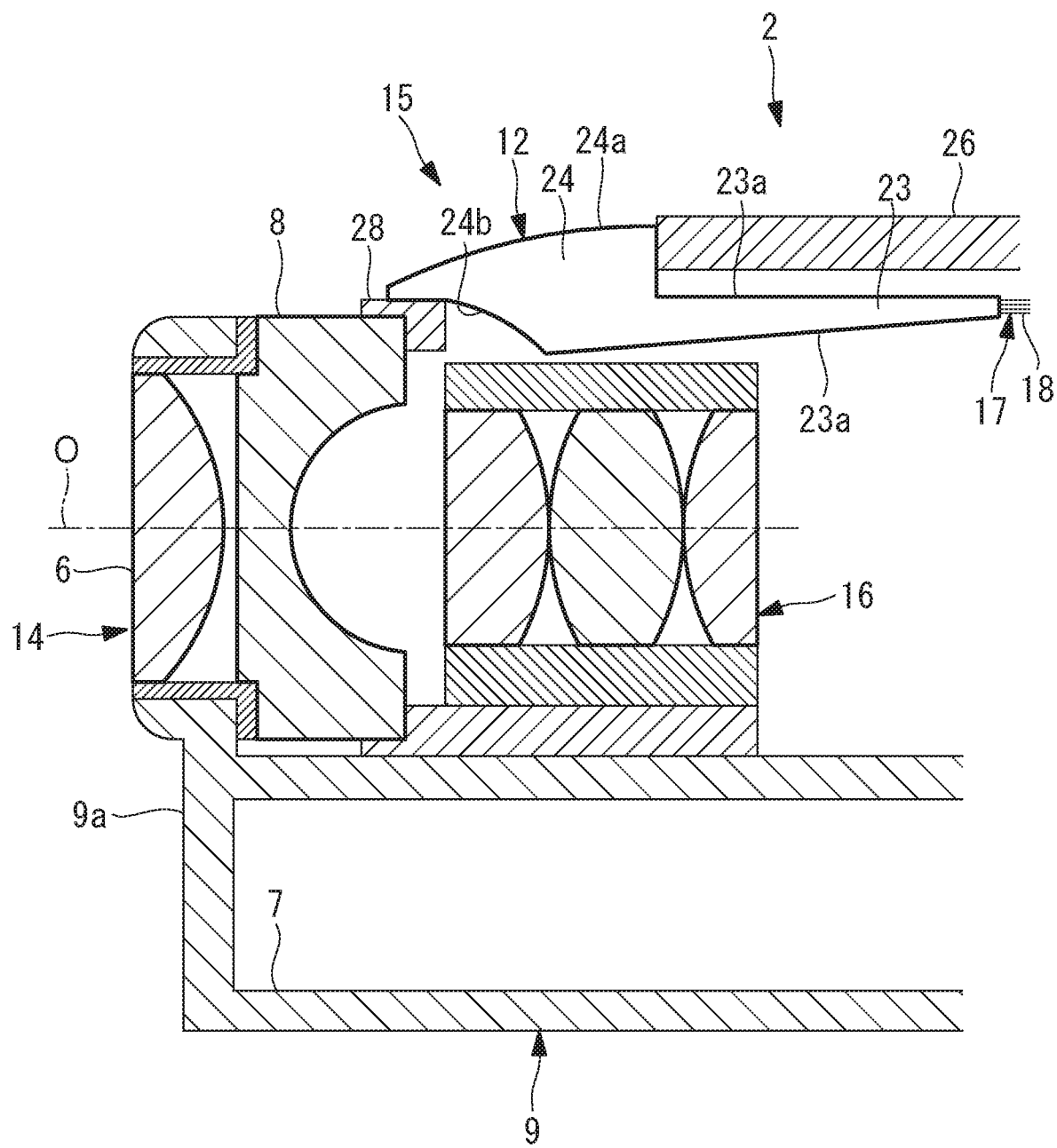
FIG. 4 is a partial longitudinal cross-sectional view showing the distal-end portion of the image-acquisition apparatus in FIG. 2.

As shown in FIGS. 2 to 4, at a distal end of the inserted portion 2, a straight-viewing forward-observation objective lens 6 is disposed facing forward at a distal-end surface 9a, and a lateral-viewing lateral-observation objective lens 8 and an illumination lens 12 are disposed in the vicinity of the forward-observation objective lens 6. Accordingly, the image-acquisition apparatus 1 according to this embodiment has a large viewing field that allows the front viewing field and the lateral viewing field to be observed simultaneously.

The forward-observation objective lens 6 is configured so as to form an image of an observation subject positioned in front of the inserted portion 2. In addition, the lateral-observation objective lens 8 is formed in a substantially columnar shape so as to form an image of an observation subject laterally positioned with respect to the inserted portion 2. The lateral-observation objective lens 8 is disposed so as to be closer to a base end of the inserted portion 2 than the forward-observation objective lens 6 is.

The inserted portion 2 is provided with: a rigid distal-end portion 9 that is provided at the most distal-end portion; a bending portion 10 that is connected to the distal-end portion 9 on a base-end side thereof; and a flexible tube portion 11 that is connected to the bending portion 10 on a base-end side thereof and that is formed of a long tubular member possessing flexibility.

As shown in FIGS. 2 and 3, a treatment-tool-channel opening 7, the forward-observation objective lens 6, the illumination lens 12, a liquid feeding nozzle 13, etc. are disposed at the distal-end surface 9a of the distal-end portion 9.

As shown in FIG. 4, an image-capturing optical system 14 and an illumination optical system 15 are disposed inside the distal-end portion 9 of the inserted portion 2. The image-capturing optical system 14 is provided with: the forward-observation objective lens 6, which is exposed at the distal-end surface 9a; the lateral-observation objective lens 8, which is exposed at a lateral surface in the periphery of the distal-end surface 9a; an imaging optical system 16 that is accommodated inside the distal-end portion 9; and an image-acquisition device (not shown) that captures an image of an observation subject, the image of which is formed by the imaging optical system 16.

A treatment-tool channel, a light guide 17, a signal cable (not shown), etc. are disposed inside the inserted portion 2. The treatment-tool channel passes through the interior of the inserted portion 2 in the longitudinal direction from the treatment-tool-channel opening 7 in the distal-end surface 9a and extends to a treatment-tool insertion port disposed in the vicinity of a connecting portion between the inserted portion 2 and the manipulating portion 3. In addition, the light guide 17 and the signal cable pass through the interior of the inserted portion 2 in the longitudinal direction from the distal-end portion 9 of the inserted portion 2, and are finally connected to the connector 5 at the terminal end of the universal cord 4 by passing through the interior of the universal cord 4 via the interior of the manipulating portion 3.

The light guide 17 is formed of a fiber bundle that is formed by bundling a plurality of light-guide fibers 18 for guiding illumination light.

An endoscope system 100 is configured by connecting, via the connector 5, a control processor 19, a light source apparatus (light source portion) 20, and a display apparatus 21, which are external apparatuses.

The manipulating portion 3 is the portion that the user grips when using the endoscope 1, and a bending manipulation knob 22 and a plurality of manipulation members corresponding to various other operations are disposed on an outer covering surface thereof. Here, for example, the bending manipulation knob 22 is a manipulation member for causing the bending portion 10 of the inserted portion 2 to be bent in arbitrary directions among up, down, left, and right directions as a result of being rotationally manipulated by the user with his/her fingers or the like.

The light source apparatus 20 is an apparatus that generates illumination light. The control processor 19 is a signal processing apparatus that performs overall control of the entire endoscope system 100. The display apparatus 21 is a display portion on which an endoscope image is displayed on the basis of image-acquisition signals acquired by the endoscope 1, and is formed of, for example, an LCD panel or the like.

The control processor 19 transmits, via the signal cable inserted so as to pass through the interior of the endoscope 1, control signals, various types of detection signals, the acquired image signals, etc. Also, the control processor 19 transfers processed image signals to the display apparatus 21, thus causing an endoscope image and various types of information, etc. to be displayed thereon. In addition, the illumination light coming from the light source apparatus 20 is guided to the illumination optical system 15 disposed in the inserted portion 2 via the universal cord 4 and the manipulating portion 3 via the connector 5, and the illumination light is radiated toward the observation subject in the surrounding area.

Figure 5:
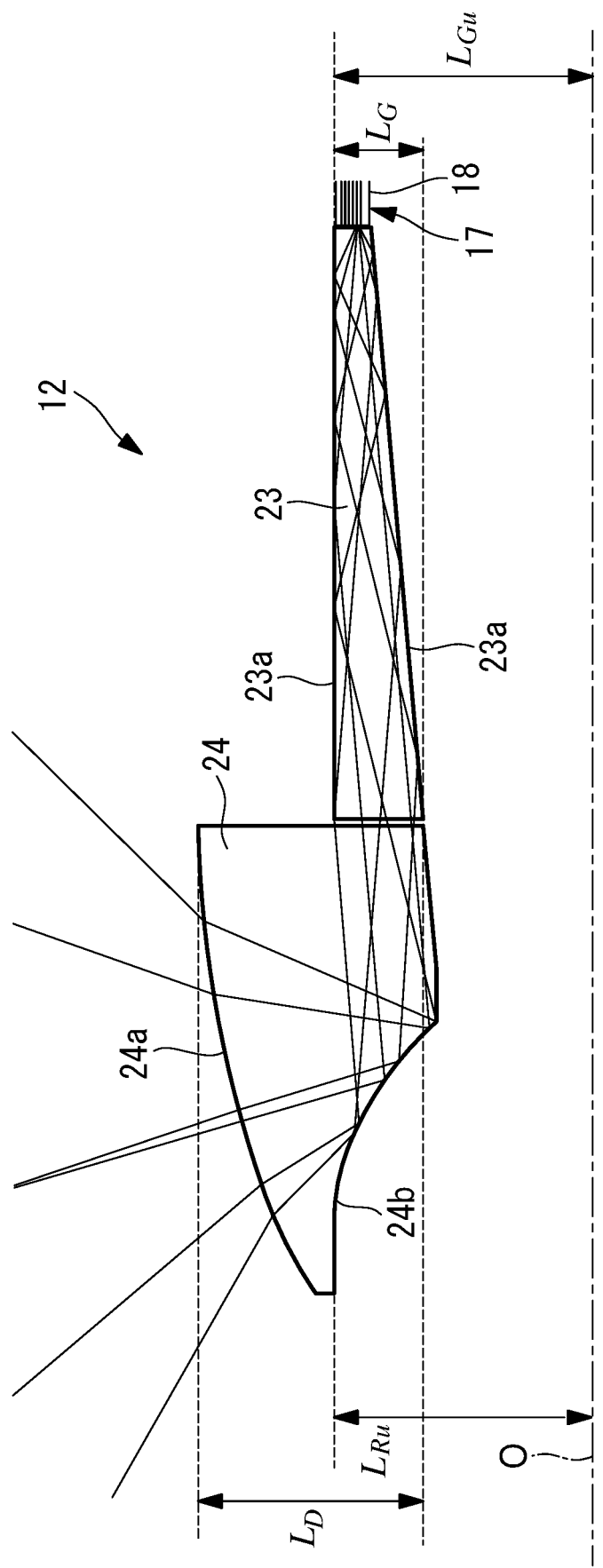
FIG. 5 is a longitudinal cross-sectional view showing an illumination optical system according to the embodiment of the present invention provided in the image-acquisition apparatus in FIG. 1.

As shown in FIG. 5, the illumination optical system 15 according to this embodiment is provided with: an illumination-light guiding portion 23 on which the illumination light guided inside the inserted portion 2 by the light guide 17 is made incident; and an illumination-light deflecting portion 24 that emits the illumination light guided by the illumination-light guiding portion 23 by deflecting the illumination light by means of reflection.

The illumination optical system 15 is disposed, so as to surround the image-capturing optical system 14, radially outward with respect to the image-capturing optical system 14 over a predetermined area in the circumferential direction centered on an optical axis O of the image-capturing optical system 14.

In one longitudinal cross-section which is a plane including the optical axis O of the image-capturing optical system 14, the illumination-light guiding portion 23 has a tapered longitudinal cross-sectional shape including two total reflection surfaces 23a that become gradually separated from each other radially inward and outward toward the distal end, in other words, in the forward traveling direction of the illumination light emitted from the light guide 17. The illumination light incident on a base-end surface of the illumination-light guiding portion 23 from the light guide 17 is guided by undergoing repeated total reflection at the two total reflection surfaces 23a while traveling inside the illumination-light guiding portion 23 toward the distal end, whereby the NA of the illumination light is gradually reduced.

In the one longitudinal cross-section which is the plane including the optical axis O of the image-capturing optical system 14, the illumination-light deflecting portion 24 is provided with: a reflection surface 24b that is disposed at a position that includes a radial region that is substantially equivalent to the illumination-light guiding portion 23; and an emission surface 24a that is disposed so as to face radially outward with respect to the reflection surface 24b. The reflection surface 24b has a convex shape facing the emission surface 24a.

The operation of the thus-configured image-acquisition apparatus 1 and illumination optical system 15 according to this embodiment will be described below.

With the illumination optical system 15 according to this embodiment, when the illumination light guided by the light guide 17 is incident on the illumination-light guiding portion 23, the illumination light undergoes repeated total reflection at the two total reflection surfaces 23a, which gradually become more distant from each other, while traveling inside the illumination-light guiding portion 23, whereby the NA of the illumination light is reduced, and the illumination light is incident on the illumination-light deflecting portion 24.

As a result of the illumination light, whose NA has been reduced in this way, being reflected by the reflection surface 24b having a convex shape, it is possible to emit, from the emission surface 24a, the illumination light over a large area after uniformly spreading out the illumination light.

As has been described above, with the illumination optical system 15 and the image-acquisition apparatus 1 according to this embodiment, because illumination over a large area is achieved only by total refection in the illumination-light guiding portion 23, reflection at the reflection surface 24b of the illumination-light deflecting portion 24, and refraction at the emission surface 24a, there is an advantage in that it is not necessary to use a diffusing material as in the related art, and thus it is possible to enhance the illumination efficiency while uniformly illuminating a large area.

By reducing the NA of the illumination light at the illumination-light guiding portion 23, the component of the light that is incident on the emission surface 24a without going via the reflection surface 24b becomes smaller. Accordingly, the totally reflected component at the emission surface 24a is reduced, which reduces the amount of unwanted light that returns toward the light guide 17, and thus, there is an advantage in that it is possible to enhance the illumination efficiency.

Furthermore, even in the case in which the illumination light has unevenness, such as color unevenness or the like, when emitted from the light guide 17, because the illumination light is mixed by undergoing repeated total reflection in the illumination-light guiding portion 23, there is also an advantage in that it is possible to reduce unevenness of the light source, such as color unevenness or the like.

Furthermore, by causing the illumination light coming from the illumination-light guiding portion 23 to be made incident at a position that is skewed radially inward in the illumination-light deflecting portion 24 by providing a step portion between the illumination-light guiding portion 23 and the illumination-light deflecting portion 24, it is possible to reduce the component of the illumination light that is incident on the emission surface 24a without going via the reflection surface 24b, and thus, it is possible to enhance the illumination efficiency.

Specifically, it is preferable that the relationship in Expression (1) below be satisfied, where the dimensional difference between radially inner and outer surfaces at the emitting end of the illumination-light guiding portion 23 is LG, and the dimensional difference between radially inner and outer surfaces at the end surface of the illumination-light deflecting portion 24 on which the illumination light is incident is LD.

$$LG \leq (3/4)LD \tag{1}$$

FIG. 5 shows, as an example, the case in which $$LG \leq (1/2)LD.$$

Here, it is preferable that Expression (2) below be satisfied:

$$(1/10)LD \leq LG \tag{2}$$

By satisfying Expression (2), it is possible to reduce the dimension LD, thus achieving a size reduction.

In addition, it is preferable that the relationship in Expression (3) below be satisfied, where the maximum radius of the reflection surface 24b from the optical axis O of the image-capturing optical system 14 is LRu, and the dimension from the optical axis O of the image-capturing optical system 14 to a radially outer surface at the emitting end of the illumination-light guiding portion 23 is LGu.

$$LGu \leq LRu \tag{3}$$

By employing such a configuration, it is possible to reduce the component of the illumination light that is incident on the emission surface 24a without going via the reflection surface 24b, and thus, it is possible to enhance the illumination efficiency. In this case, it is more preferable that the relationship be as follows:

$$LGu < LRu.$$

Note that the illumination optical system 15 according to the present invention can be modified in the following ways.

Figure 6:
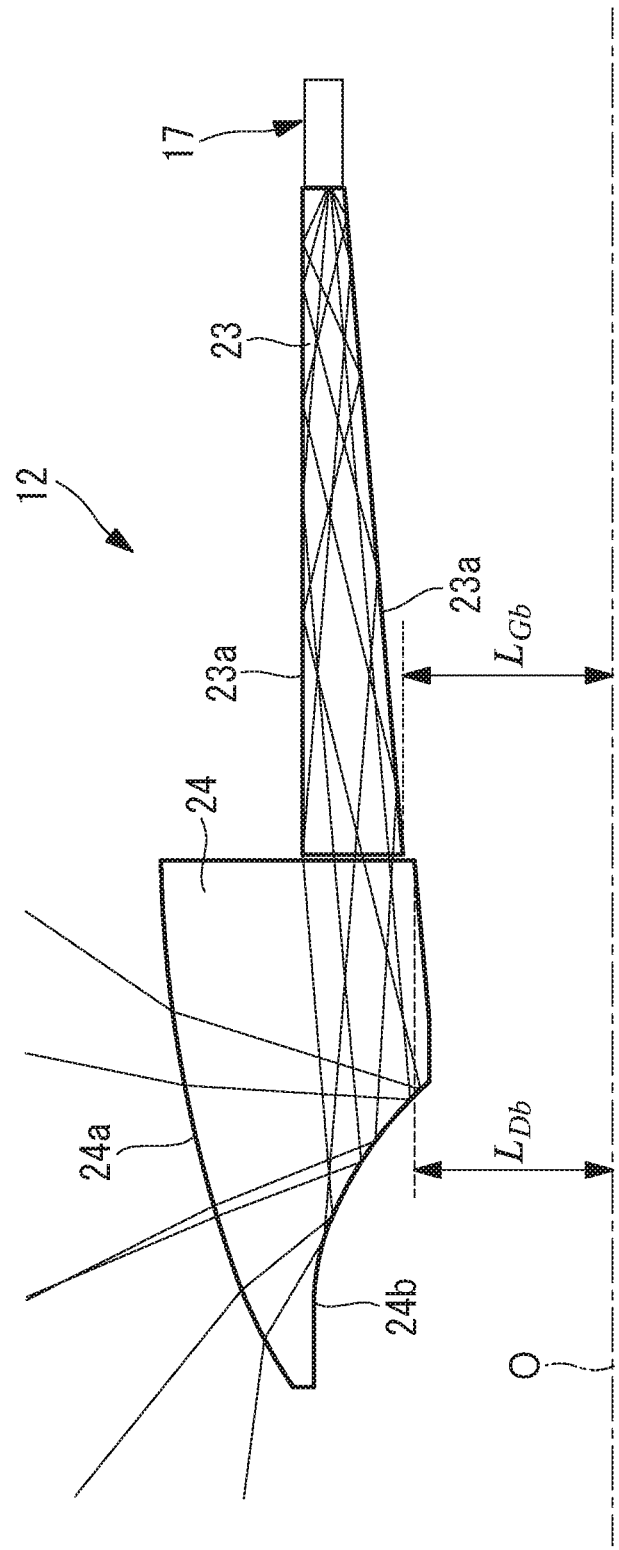
FIG. 6 is a longitudinal cross-sectional view showing a first modification of the illumination optical system in FIG. 5.

Although the case in which the positions of the radially inner surfaces of the illumination-light guiding portion 23 and the illumination-light deflecting portion 24 are aligned at the position at the emitting end of the illumination-light guiding portion 23 of the illumination optical system 15 is shown in FIG. 5 as an example, alternatively, as shown in FIG. 6, the position of the radially inner surface of the illumination-light guiding portion 23 may be disposed radially further outward than the radially inner surface of the illumination-light deflecting portion 24 is.

In other words, the relationship may be as follows:

$$LDb \leq LGb \tag{4}$$

In this case, it is more preferable that the relationship be as follows:

LDb<LGb.

Here, LDb is the radial dimension of a radially inner surface in the incident surface of the illumination-light deflecting portion 24, and LGb is the radial dimension of the radially inner surface at the emitting end of the illumination-light guiding portion 23.

By doing so, it is possible to prevent a reduction in efficiency caused by leaking of the illumination light emitted from the illumination-light guiding portion 23 radially inward toward the image-capturing optical system 14 without being incident on the illumination-light deflecting portion 24.

Figure 7:
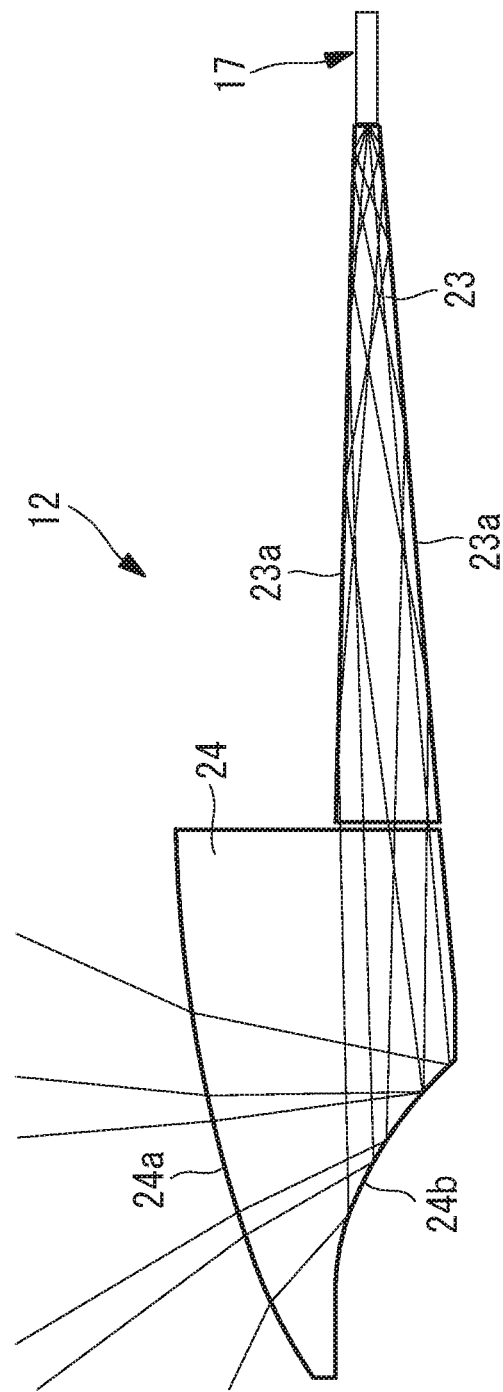
FIG. 7 is a longitudinal cross-sectional view showing a second modification of the illumination optical system in FIG. 5.

Although, in FIGS. 5 and 6, the illumination-light guiding portion 23 is formed in a tapered shape by inclining only the radially inner surface of the illumination-light guiding portion 23 with respect to the optical axis O, alternatively, as shown in FIG. 7, both the radially inner surface and outer surface of the illumination-light guiding portion 23 may be inclined with respect to the optical axis O. By employing such a configuration, it is possible to further reduce the NA of the illumination light when made incident on the reflection surface 24b, and thus, it is possible to enhance the illumination efficiency by further reducing the amount of the illumination light that is made incident on the emission surface 24a without going via the reflection surface 24b. Only the radially outer surface of the illumination-light guiding portion 23 may be inclined with respect to the optical axis O.

Figure 8:
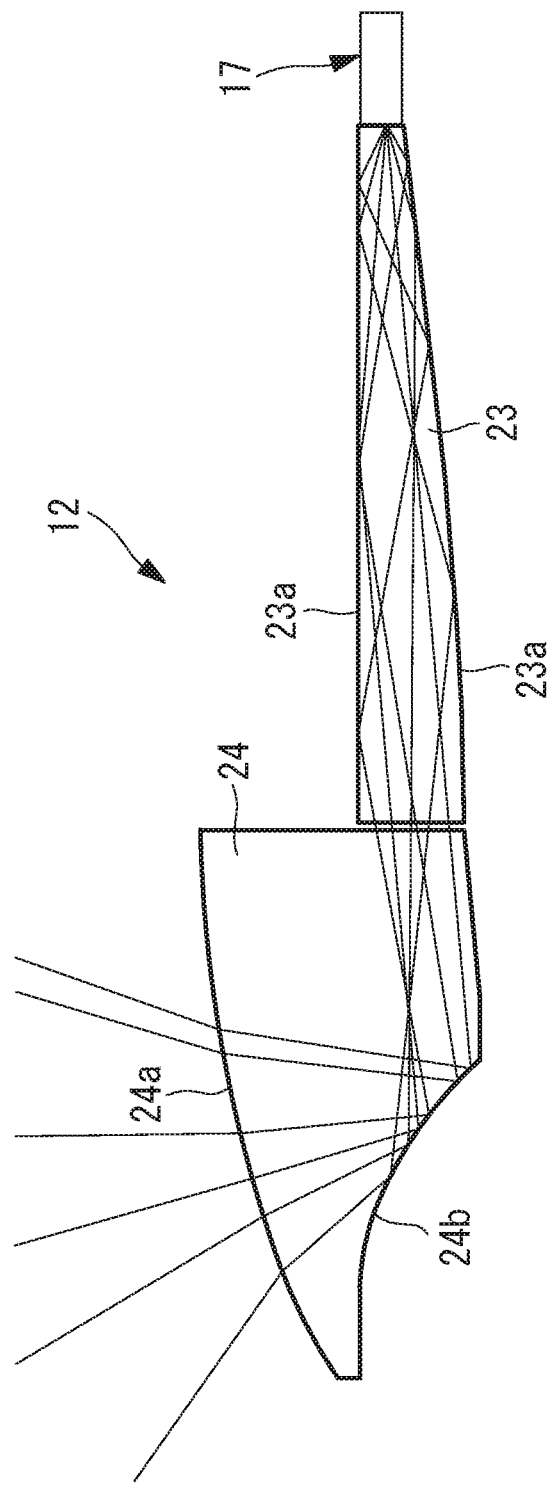
FIG. 8 is a longitudinal cross-sectional view showing a third modification of the illumination optical system in FIG. 5.

As shown in FIG. 8, at least one of the total reflection surfaces 23a may have curvature at least in a portion thereof.

By doing so, it is possible to change the NA of the illumination light emitted from the emitting end of the illumination-light guiding portion 23. In addition, it is possible to efficiently mix the illumination light, and thus, there is an advantage in that it is possible to reduce the axial length of the illumination-light guiding portion 23.

Figure 9:
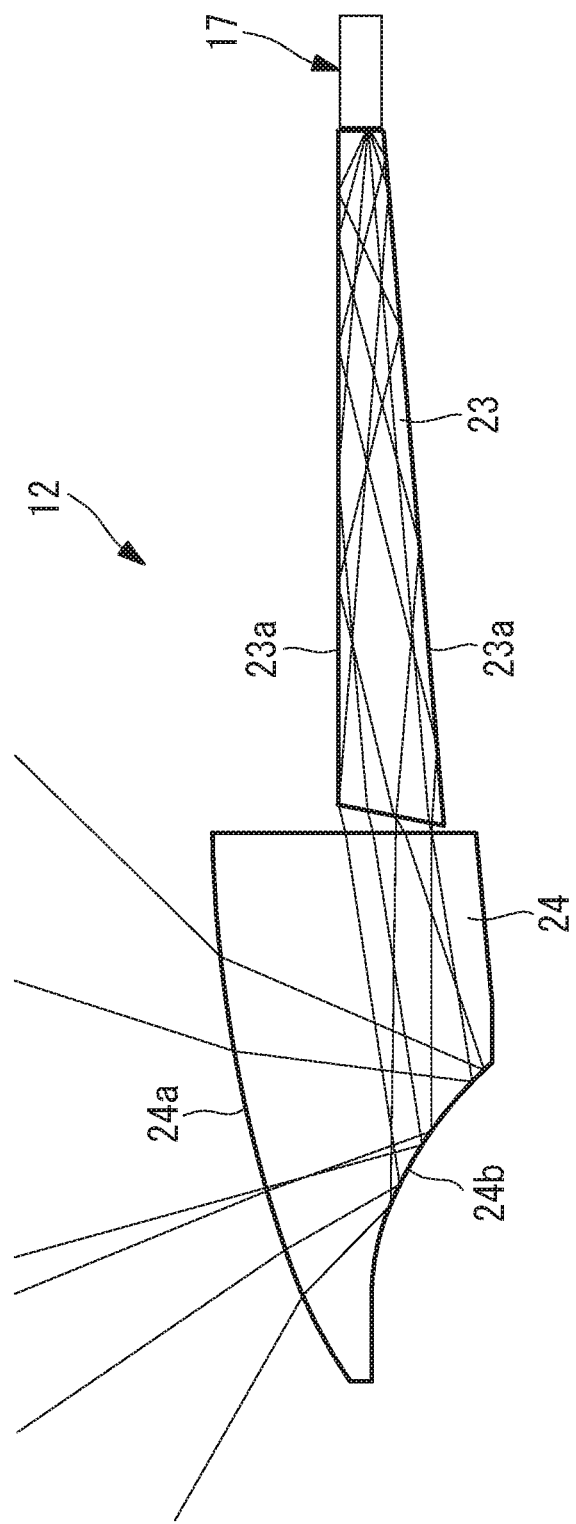
FIG. 9 is a longitudinal cross-sectional view showing a fourth modification of the illumination optical system in FIG. 5.

As shown in FIG. 9, the emitting end of the illumination-light guiding portion 23 may be inclined so as to be tilted radially outward toward the base end. By employing such a configuration, the illumination light emitted from the emitting end of the illumination-light guiding portion 23 is deflected in such a direction that the illumination light approaches the optical axis O due to refraction at the emitting end. As a result, it is possible to reduce the amount of the illumination light that is incident on the emission surface 24a without going via the reflection surface 24b, and thus, there is an advantage in that it is possible to enhance the illumination efficiency.

Figure 10:
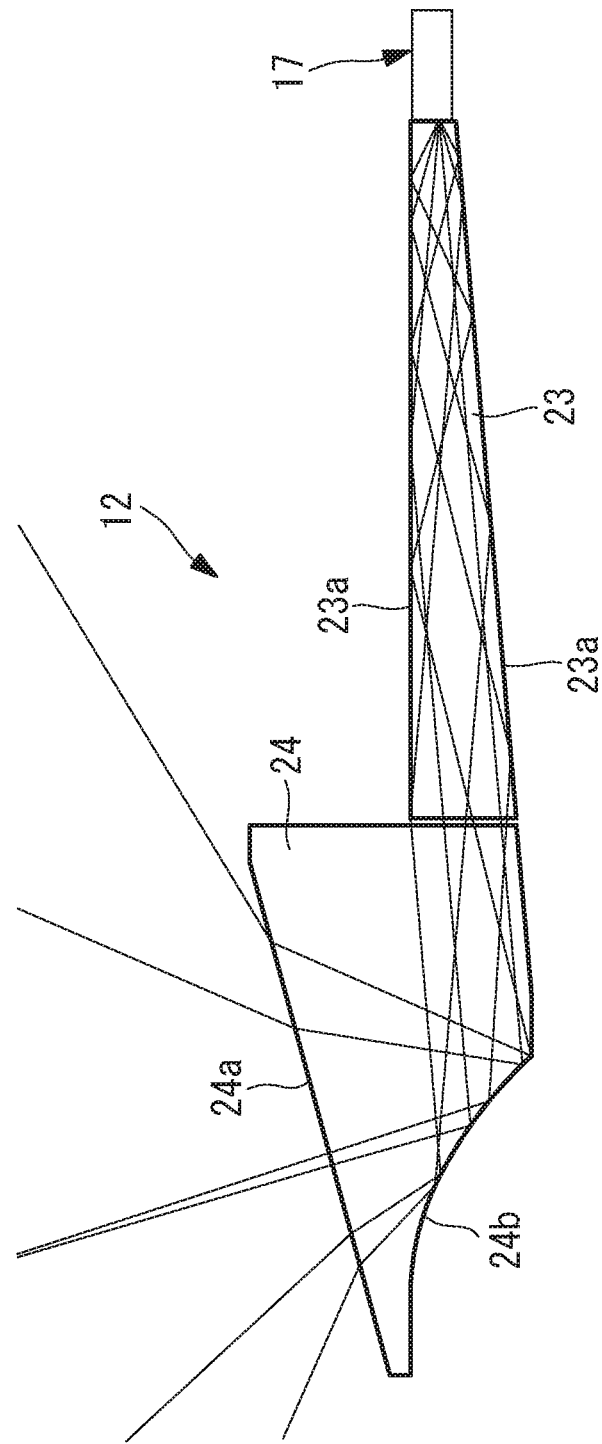
FIG. 10 is a longitudinal cross-sectional view showing a fifth modification of the illumination optical system in FIG. 5.

Although a curved surface having a radially outward convex shape is shown in FIGS. 5 to 9 as an example of the emission surface 24a of the illumination-light deflecting portion 24, alternatively, as shown in FIG. 10, the emission surface 24a may be formed of a conical surface whose diameter decreases toward the distal end. By employing such a configuration, it is possible to increase the spread of the illumination light due to refraction at the emission surface 24a, and thus, it is possible to supply the illumination light to a larger area.

It is desirable that the illumination-light guiding portion 23 and the illumination-light deflecting portion 24 be formed of separate prisms, and that these components be bonded together by using a transparent adhesive or the like. By bonding together the illumination-light guiding portion 23 and the illumination-light deflecting portion 24, it is possible to reduce the Fresnel reflection at the interface between the illumination-light guiding portion 23 and the illumination-light deflecting portion 24, as compared to the case in which these components are not glued together, and thus, it is possible to enhance the illumination efficiency. In the case of FIG. 9, because bonding eliminates the effect of the inclination of the emitting end, it is desirable that said components not be glued together.

The materials used for the illumination-light guiding portion 23 and the illumination-light deflecting portion 24 may be the same or different. For example, it is desirable that the materials be selected so that the refractive index of the illumination-light guiding portion 23 is less than the refractive index of the illumination-light deflecting portion 24.

By employing such a configuration, it is possible to further reduce the NA of the illumination light emitted from the illumination-light guiding portion 23 due to refraction when the illumination light is incident on the illumination-light deflecting portion 24.

Because of this, it is possible to enhance the illumination efficiency by reducing the amount of illumination light that is incident on the emission surface 24a without going via the reflection surface 24b. In addition, because the emission surface 24a of the illumination-light deflecting portion 24 is exposed at the surface of the endoscope 1, from the viewpoint of biocompatibility, drug resistance, etc., the materials that can be used in the illumination-light deflecting portion 24 are limited.

Since the illumination-light guiding portion 23 is not exposed at the surface, there is some freedom in terms of material selection. From such a viewpoint also, different materials may be used for the illumination-light deflecting portion 24 and the illumination-light guiding portion 23.

Figure 11:
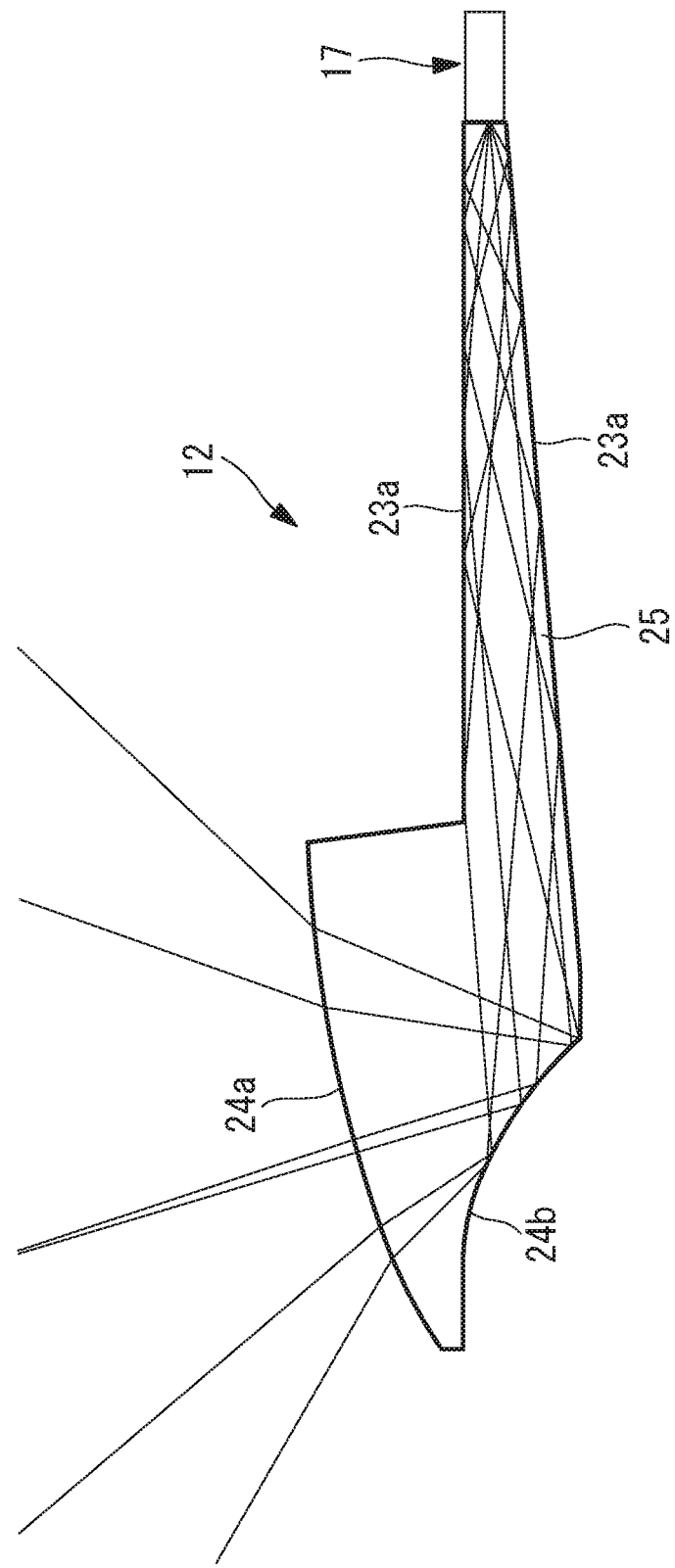
FIG. 11 is a longitudinal cross-sectional view showing a sixth modification of the illumination optical system in FIG. 5.

As shown in FIG. 11, the illumination-light guiding portion 23 and the illumination-light deflecting portion 24 may be formed of an integral prism 25. By integrally forming the illumination-light guiding portion 23 and the illumination-light deflecting portion 24, high efficiency is achieved because the loss due to the Fresnel reflection at the interface between the illumination-light guiding portion 23 and the illumination-light deflecting portion 24 is eliminated.

Furthermore, there is also an effect of reducing the number of components in the illumination unit.

The step portion formed between the illumination-light deflecting portion 24 and the illumination-light guiding portion 23 may be perpendicular or inclined with respect to the optical axis O. Because the illumination light does not pass through this step portion, it is possible to change, as appropriate, the step portion depending on the structure of a frame 26 for securing the illumination optical system 15.

Figure 12A:
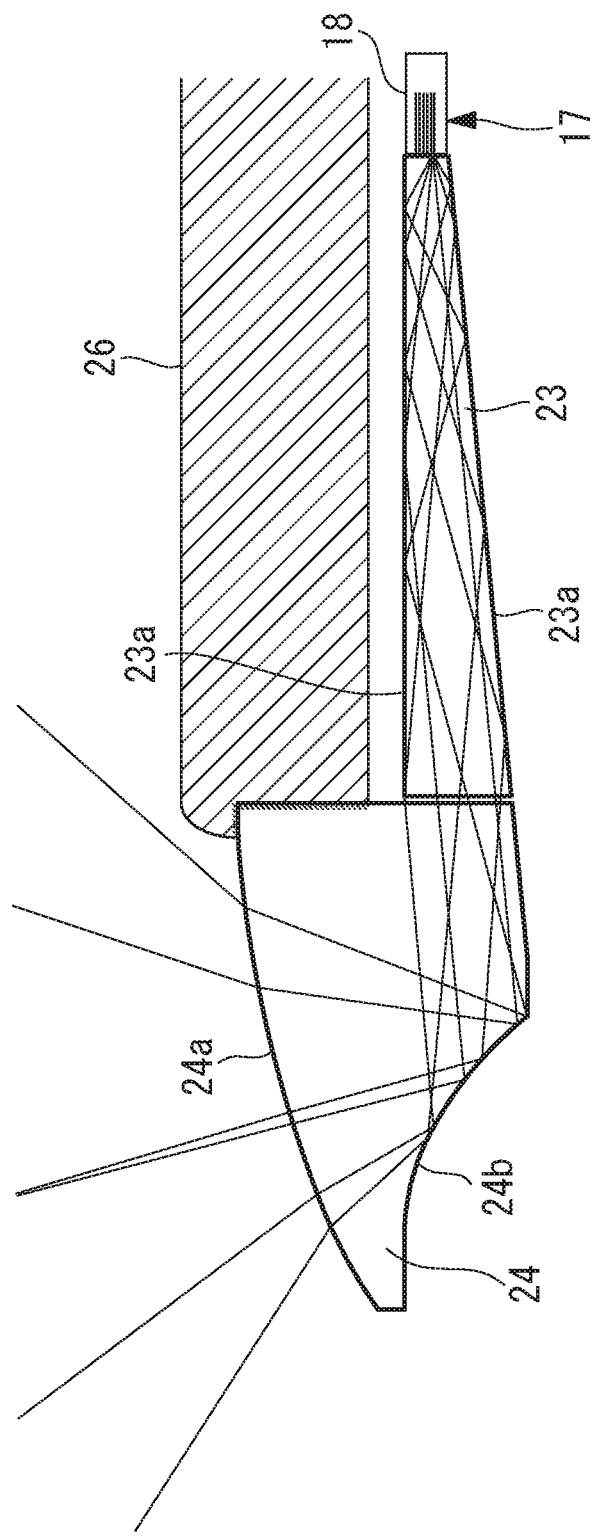
FIG. 12A is a longitudinal cross-sectional view showing the relationship between the illumination optical system in FIG. 5 and an example frame.

FIG. 12A shows an example of the frame 26 for securing the illumination optical system 15.

In the case in which the relationship in Expression (1) is satisfied, because the step portion creates, on the incident-surface side of the illumination-light deflecting portion 24, a portion on which the illumination light is not incident, as shown in FIG. 12A, it is possible to utilize this portion as a surface to be bonded to the frame 26 for securing the illumination optical system 15.

By employing such a configuration, it is possible to secure the illumination optical system 15 by using the frame 26 without reducing the illumination efficiency.

Figure 12B:
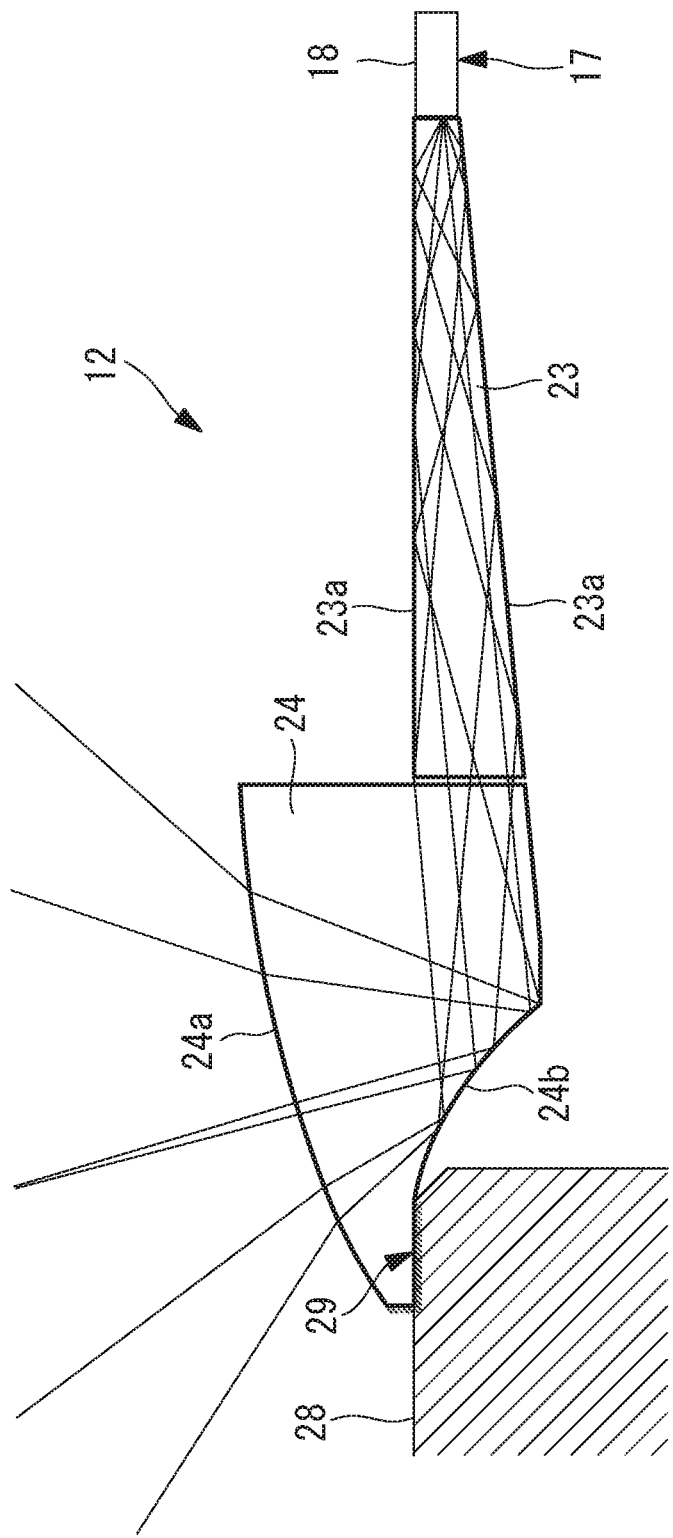
FIG. 12B is a longitudinal cross-sectional view showing the relationship between the illumination optical system in FIG. 5 and another example frame.

As shown in FIG. 12B, the frame 28 that secures the lateral-observation objective lens 8 or the imaging optical system 16 and a portion of the illumination-light deflecting portion 24 may be bonded and secured to each other. As an adhesive, for example, a black adhesive may be used, thus forming an illumination-light absorbing portion (absorbing member) 29. By providing the illumination-light absorbing portion 29, it is possible to prevent the illumination light from directly being incident on the lateral-observation objective lens 8.

Figure 13A:
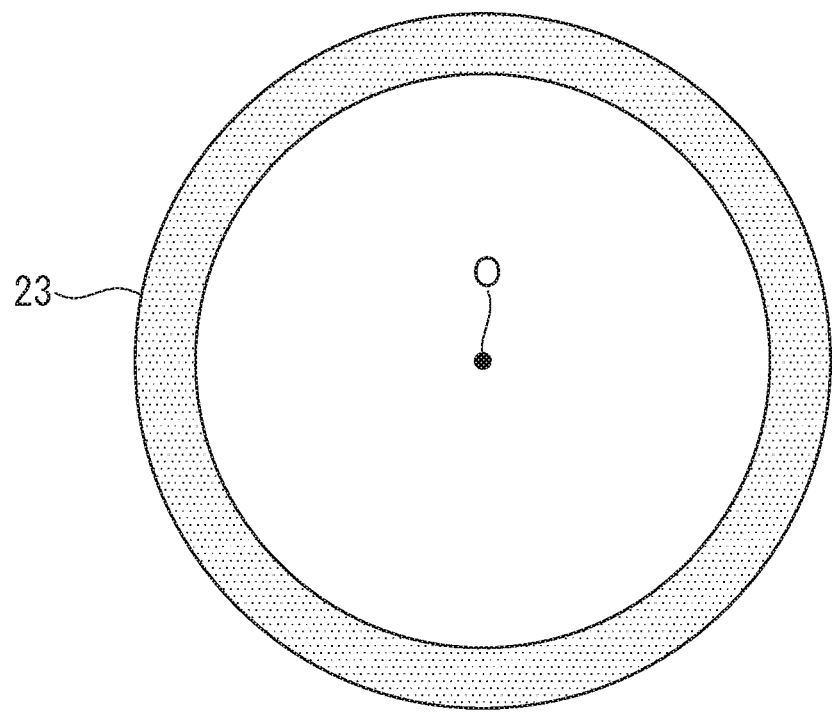
FIG. 13A is a lateral cross-sectional view showing an example of an illumination-light guiding portion of the illumination optical system in FIG. 5.

As shown in FIG. 13A, it is preferable that the illumination-light guiding portion 23 be formed as a complete solid of revolution disposed over the entire circumference about the optical axis O of the image-capturing optical system 14, because doing so allows the illumination light to be uniformly guided around the entire circumference. However, as shown in FIGS. 2 and 3, the endoscope 1 is generally configured such that the liquid feeding nozzle 13, etc. are disposed at portions in the circumferential direction of the lateral-observation objective lens 8, and, in that case, a portion of the lateral viewing field is missing.

Figure 13B:
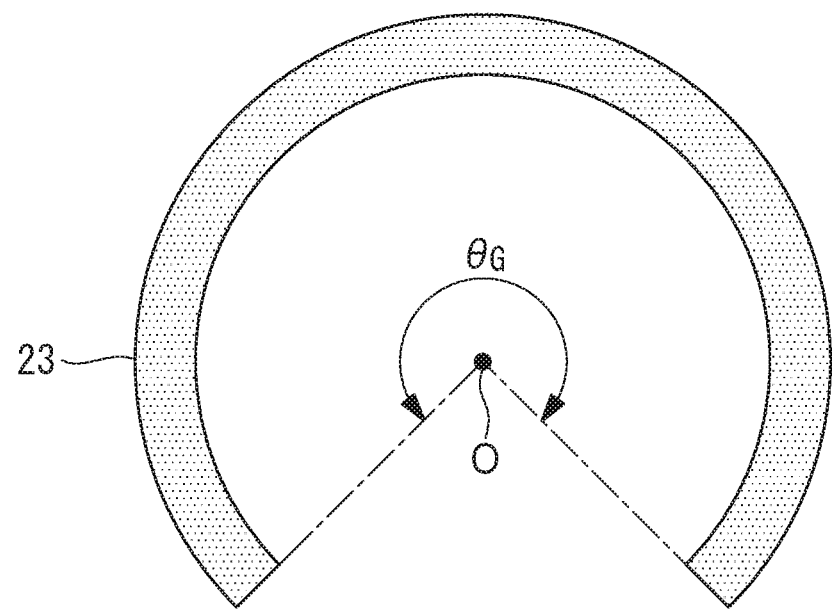
FIG. 13B is a lateral cross-sectional view showing another example of the illumination-light guiding portion of the illumination optical system in FIG. 5.

In this case, as shown in FIG. 13B, it is desirable that the illumination-light guiding portion 23 be provided in the circumferential direction within an angular range $\theta G \leq 300°$. In addition, although it has been described that the optical axis O of the image-capturing optical system 14 is the center axis of the illumination-light guiding portion 23 in this embodiment, there is no limitation thereto, and the axis may be eccentric.

Figure 14:
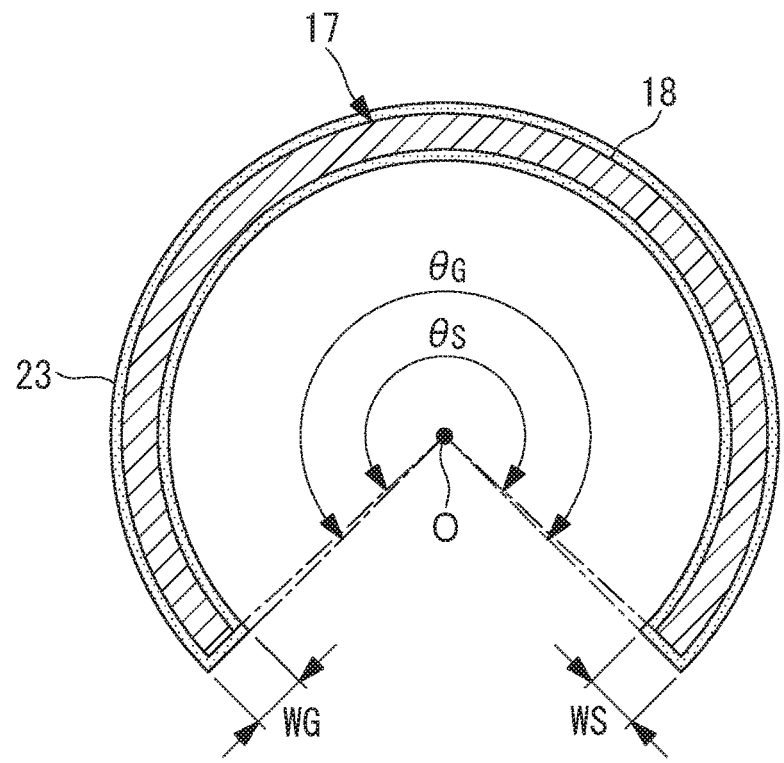
FIG. 14 is a lateral cross-sectional view showing an example of the positional relationship between the illumination-light guiding portion in FIG. 13B and a light guide.

FIG. 14 shows an example in which the cylindrical light guide 17 in which a portion thereof in the circumferential direction is cut out is arranged about the optical axis of O of the image-capturing optical system 14 serving as the center axis. In order to efficiently make the illumination light emitted from the light guide 17 incident on the illumination—light guiding portion 23, it is preferable that an angle $\theta S$ in the circumferential direction of the light guide 17 satisfy the relationship below:

$\theta S \leq \theta G$.

It is preferable that a width WG of the incident surface of the illumination-light guiding portion 23 and a width WS of the annular light guide 17 satisfy the relationship below:

$WS \leq WG$.

As shown in FIG. 14, by setting the shape of the light guide 17 so as to be substantially equivalent to the shape of the incident surface of the illumination-light guiding portion 23, and by setting the size thereof to be slightly smaller, it is possible to uniformly guide the illumination light into the interior of the illumination-light guiding portion 23, and, as a result, it is possible of uniformly supply illumination light.

Figure 15:
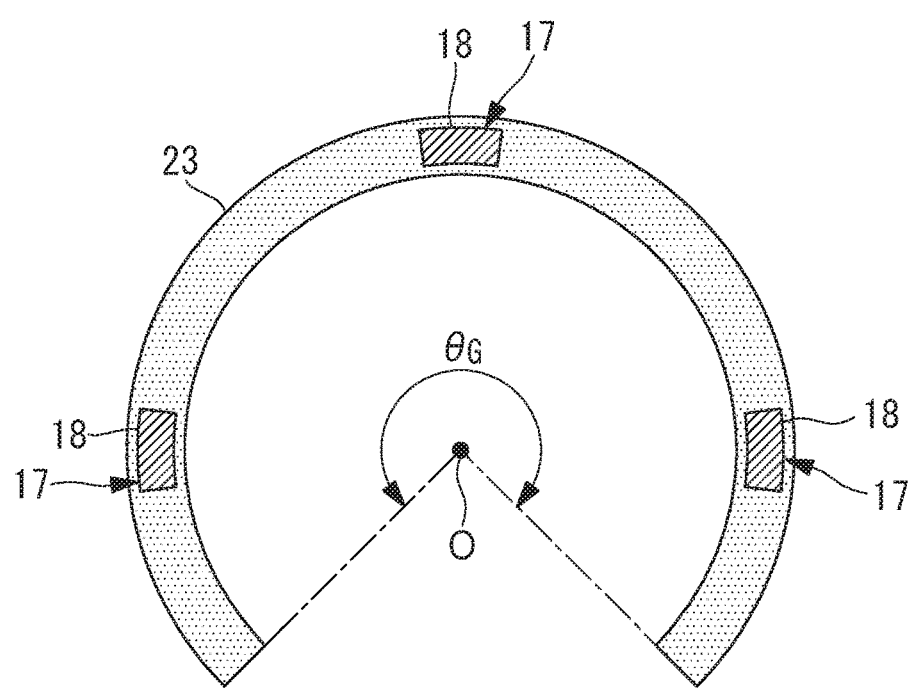
FIG. 15 is a lateral cross-sectional view showing another example of the positional relationship between the illumination-light guiding portion in FIG. 13B and light guides.

FIG. 15 shows an example in which, in the illumination-light guiding portion 23 shown in FIG. 13B, at least two light guides 17 are disposed, in the circumferential direction with a space therebetween, in the incident surface of the illumination-light guiding portion 23. Unlike the case in FIG. 14, it is not necessary to cylindrically arrange the light guides 17. Because the illumination light emitted from the light guides 17 is guided inside the illumination-light guiding portion 23 while also being spread in the circumferential direction, it is possible to achieve uniform illumination even in the case in which the emission surfaces of the light guides 17 are smaller as compared to the incident surface of the illumination-light guiding portion 23.

Figure 16:
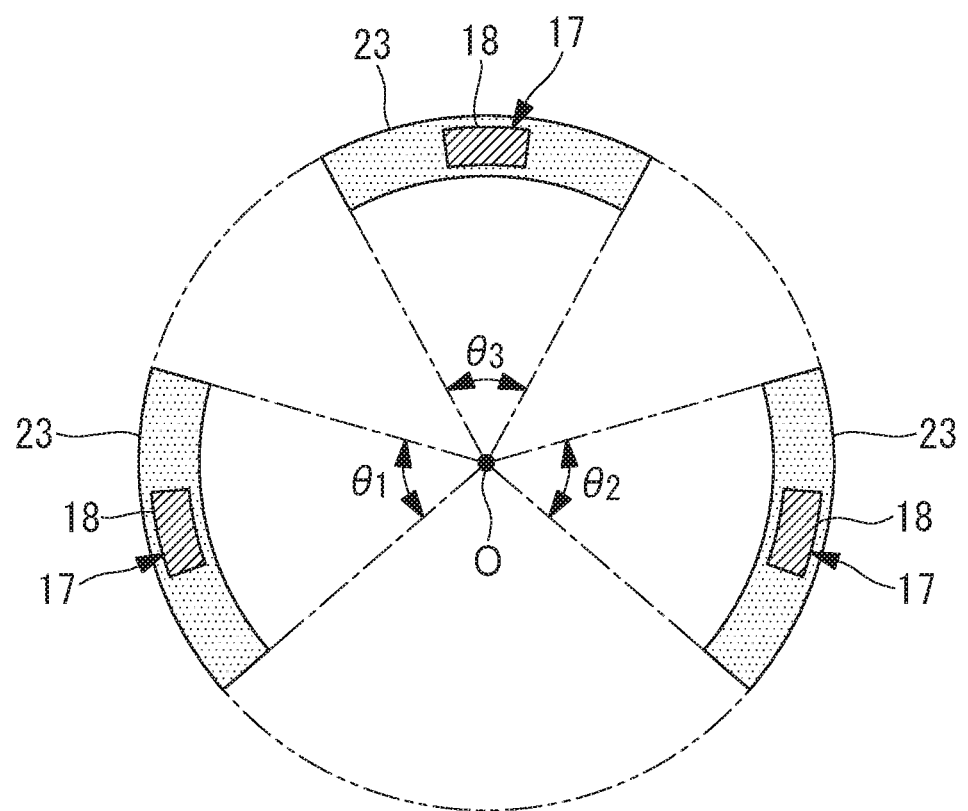
FIG. 16 is a lateral cross-sectional view showing another example of the illumination-light guiding portion in FIG. 13B.

The illumination-light guiding portion 23 need not have the structure of a single solid of revolution. Specifically, as shown in FIG. 16, a plurality of illumination-light guiding portions 23 having arc-shaped lateral cross-sections centered on the optical axis O of the image-capturing optical system 14 may be disposed in the circumferential direction with spaces therebetween. FIG. 16 shows, as an example, a case in which the angles of the individual illumination-light guiding portions 23 in the circumferential direction are $\theta 1$, $\theta 2$, and $\theta 3$.

Figure 17A:
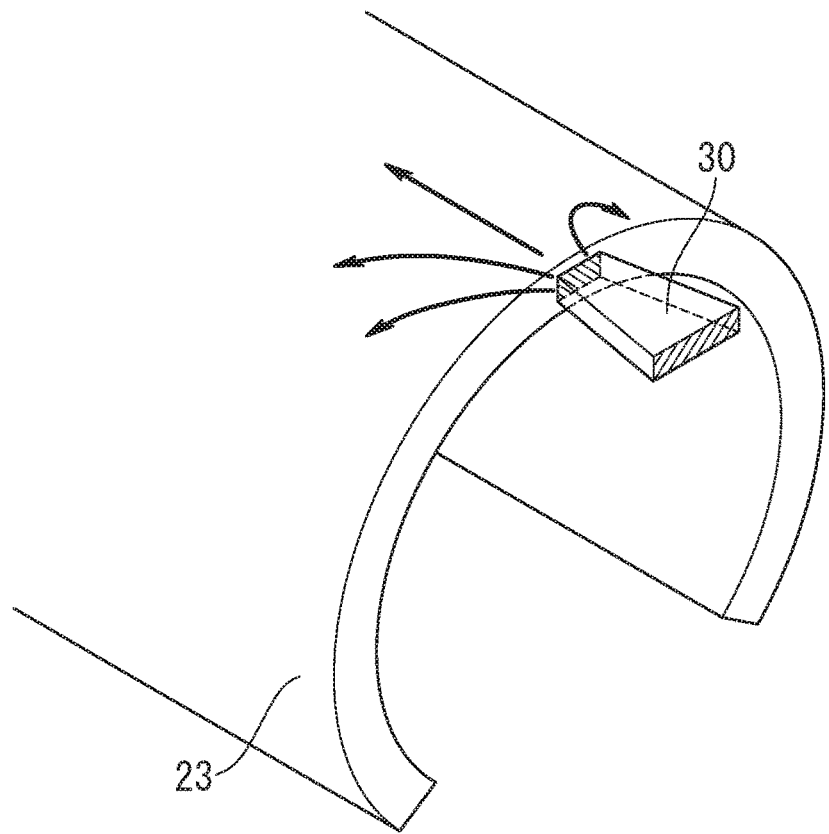
FIG. 17A is a perspective view showing an example of a second illumination-light guiding portion disposed between the illumination-light guiding portion in FIG. 13B and a light guide.

As shown in FIG. 17A, a second illumination-light guiding portion 30 may be disposed between the light guide 17 and the illumination-light guiding portion 23.

Figure 17B:
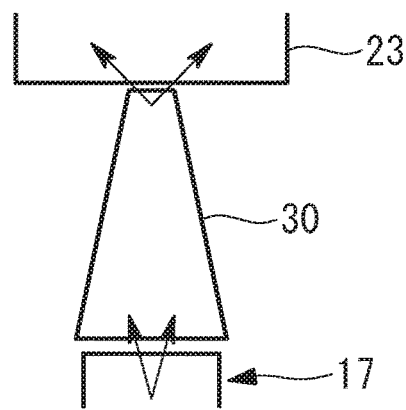
FIG. 17B is a diagram in which the second illumination-light guiding portion in FIG. 17A is viewed from a radial direction.
Figure 17C:
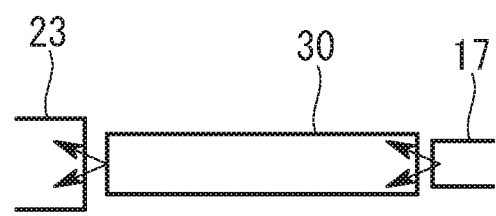
FIG. 17C is a diagram in which the second illumination-light guiding portion in FIG. 17A is viewed from a tangential direction.

FIG. 17A is a perspective view in which the second illumination-light guiding portion 30 is connected to the illumination-light guiding portion 23 in FIG. 13; FIG. 17B is a plan view showing the illumination-light guiding portion 23 in FIG. 13, the second illumination-light guiding portion 30, and the light guide 17; and FIG. 17C is a side view showing the illumination-light guiding portion 23 in FIG. 13, the second illumination-light guiding portion 30, and the light guide 17.

The second illumination-light guiding portion 30 has an incident surface on which the illumination light is incident and an emission surface from which the illumination light is emitted, and has a tapered shape in which the lateral cross-sectional area gets smaller toward the emission surface from the incident surface. By connecting the second illumination-light guiding portion 30 having such a shape, it is possible to spread out the illumination light when being made incident on the illumination-light guiding portion 23, and thus, it is possible to uniformly guide the illumination light in the circumferential direction inside the illumination-light guiding portion 23.

As shown in FIGS. 15 and 16, this configuration is suitable in the case in which the sizes of the light guides 17 are smaller than that of the incident surface of the illumination-light guiding portion 23.

As shown in FIGS. 18A, 18B, 18C, and 19, a similar effect may be achieved by means of the shape of the incident surface of illumination-light guiding portion 23, without employing the second illumination-light guiding portion 30.

Figure 18A:
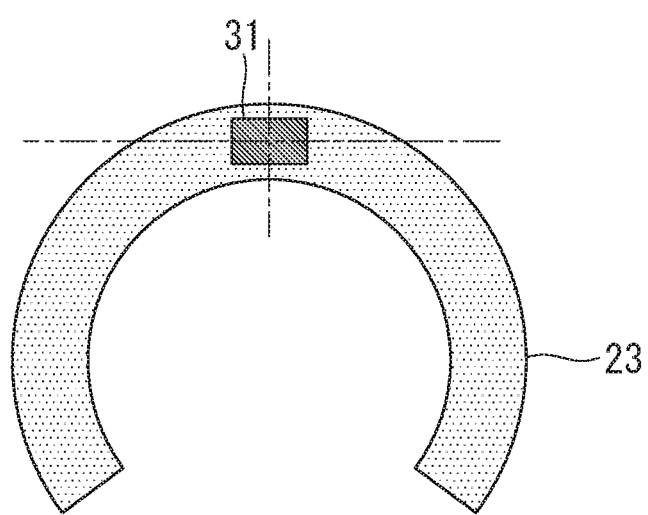
FIG. 18A is a front view for explaining a deflecting portion provided at an incident end surface of the illumination-light guiding portion in FIG. 13B.
Figure 18B:
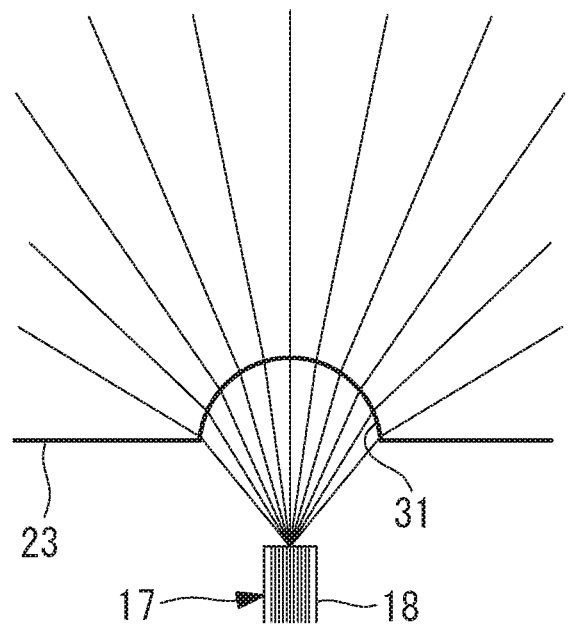
FIG. 18B is a diagram in which the deflecting portion in FIG. 18A is viewed from a radial direction.

In other words, as shown in FIG. 18B, a deflecting portion 31 that has a semicircular shape in the circumferential direction and that is formed of a concave surface radially depressed by a certain thickness dimension may be provided at least in a portion of the incident end surface of the illumination-light guiding portion 23.

Figure 18C:
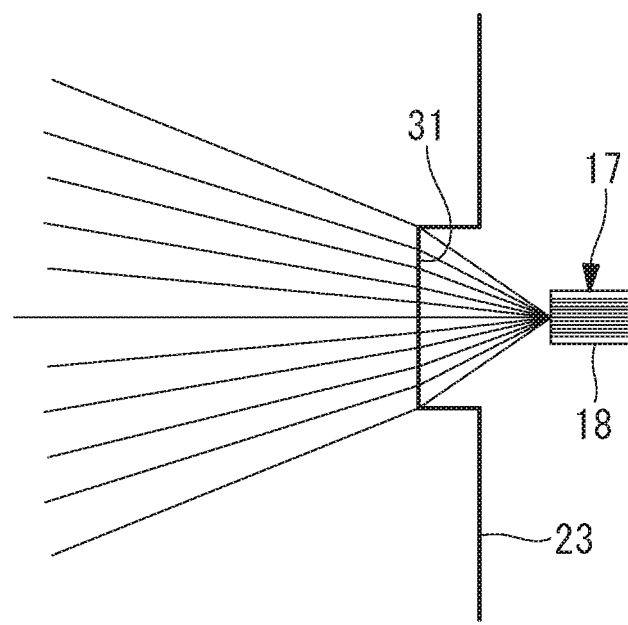
FIG. 18C is a diagram in which the deflecting portion in FIG. 18B is viewed from a tangential direction.
Figure 19:
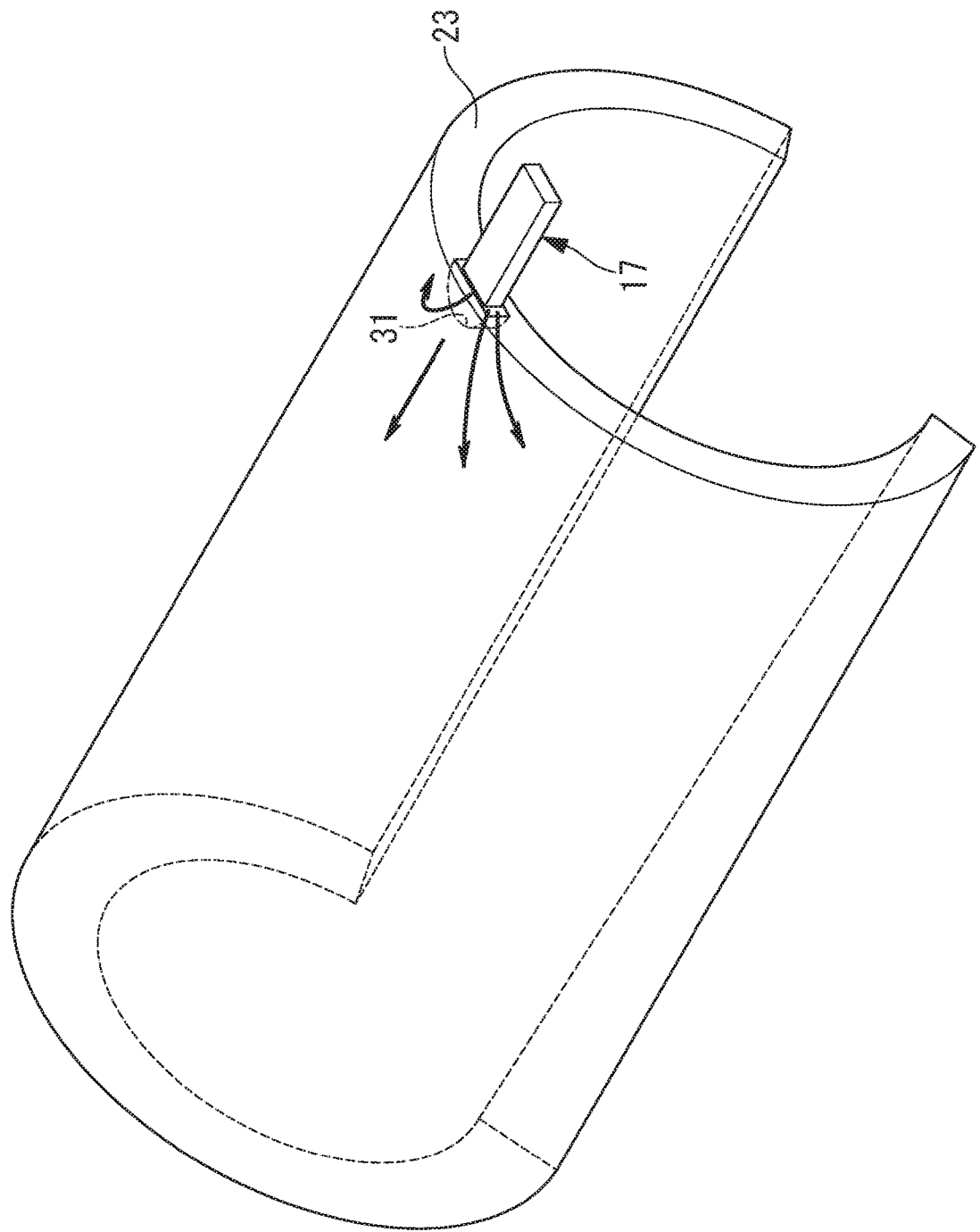
FIG. 19 is a perspective view showing the illumination-light guiding portion, which has the deflecting portion in FIG. 18A, and a light guide.

Such a deflecting portion 31 has an effect of increasing the NA of the illumination light in the circumferential direction, as shown in FIG. 18B, and has an effect of reducing the NA of the illumination light in the radial direction, as shown in FIG. 18C. Accordingly, there is an advantage in that, by spreading out the illumination light emitted from the light guide 17 in the circumferential direction of the illumination-light guiding portion 23, it is possible to uniformly guide the illumination light inside the illumination-light guiding portion 23.

The shape of the deflecting portion 31 is not limited to the semicircular shape, and it is possible to employ a member having an arbitrary shape, such as a partial arc shape, a rectangular shape, a triangular shape, a trapezoidal shape, or the like.

In addition, although an example in which the deflecting portion 31 is provided at one location in the circumferential direction has been described as an example, a plurality of deflecting portions 31 may be disposed in the circumferential direction with spaces therebetween.

Figure 20:
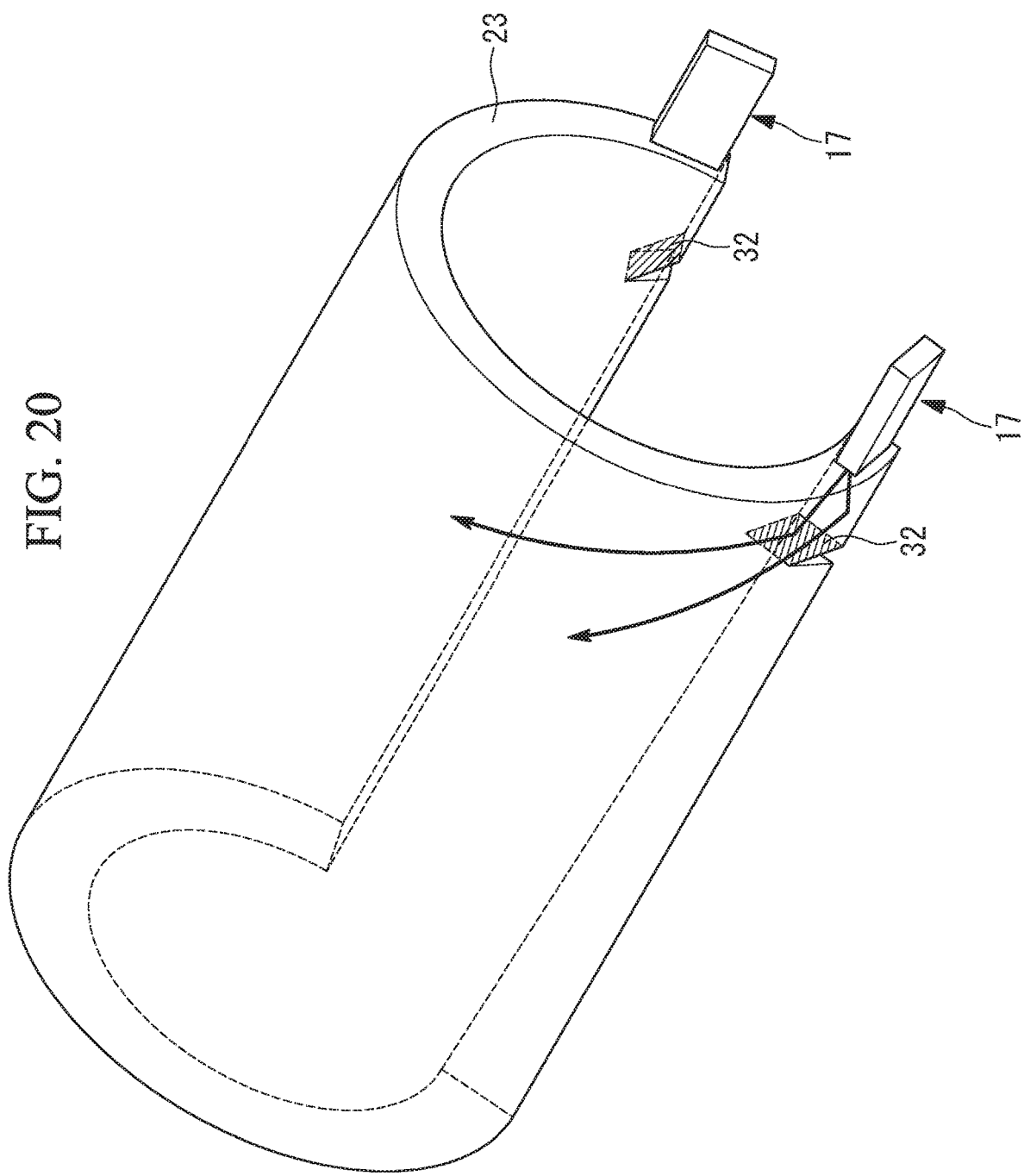
FIG. 20 is a perspective view showing the illumination-light guiding portion, which has other deflecting portions at end surfaces in circumferential directions, and light guides.

As shown in FIG. 20, in the illumination-light guiding portion 23 having a cylindrical shape in which a portion thereof is cut out, deflection surfaces 32 formed of inclined surfaces that are inclined forward may be provided at end surfaces of the illumination-light guiding portion 23 in the circumferential directions, and the light guides 17 may be disposed so that the illumination light coming from the light guides 17 is incident in such a manner that the illumination light travels toward the deflection surfaces 32. By doing so, the illumination light is deflected in the circumferential direction of the illumination-light guiding portion 23, which allows the illumination light to be guided in a spiraling manner, and thus, it is possible to generate uniform illumination light. Because an effect of spreading out the illumination light in the circumferential direction of the illumination-light guiding portion 23 is also achieved in this case, this configuration is suitable in the case in which the sizes of the light guides 17 are smaller than that of the incident end surface of the illumination-light guiding portion 23.

The reflection surface 24b of the illumination-light deflecting portion 24 and the deflection surfaces 32 in FIG. 20 may be coated with a metal (for example, aluminum or silver), a dielectric multi-layer film, or an oxide multi-layer film, thus increasing the reflectance thereof.

In addition, although an example in which the illumination light coming from the light source apparatus 20 is guided by using the light guide 17 has been described, there is no limitation thereto, and other light source portions, such as an LED, a laser light source, etc., may be employed.

As a result, the above-described embodiment leads to the following aspects.

An aspect of the present invention is an illumination optical system comprising: an illumination-light guiding portion configured to guide illumination light emitted from a light source portion; and an illumination-light deflecting portion configured to emit the illumination light guided thereto by the illumination-light guiding portion after deflecting the illumination light by means of reflection; wherein, in one cross-section along a direction in which the illumination light travels, the illumination-light guiding portion has a pair of total reflection surfaces in which the distance therebetween gradually increases in a forward traveling direction of the illumination light, and the illumination-light deflecting portion is provided with an emission surface from which the illumination light guided by the illumination-light guiding portion is emitted, and a reflection surface that has a convex shape facing the emission surface and that reflects the illumination light guided by the illumination-light guiding portion toward the emission surface.

With this aspect, the illumination light emitted from the light source portion is guided by the illumination-light guiding portion and is subsequently emitted from the illumination-light deflecting portion after being deflected by means of reflection. When being guided by the illumination-light guiding portion, because the illumination light is guided while undergoing total reflection at the pair of total reflection surfaces having the shapes that gradually become more distant from each other in the forward traveling direction of the illumination light, it is possible to reduce the NA while the light is being guided, and thus, it is possible to efficiently make the illumination light incident on the reflection surface. Also, as a result of the illumination light being emitted to the exterior by being refracted at the emission surface after being spread out as a result of reflection at the reflection surface having the convex shape, it is possible to illuminate a large area. In other words, because the illumination depends only on total reflection, reflection, and refraction, it is possible to enhance the illumination efficiency while uniformly illuminating a large area.

In the above-described aspect, the illumination-light guiding portion may have an emitting end from which the guided illumination light is emitted, and the reflection surface may be disposed at a position facing the emitting end.

By doing so, when the illumination light emitted from the illumination-light guiding portion, in which the NA has been reduced, is made incident on the emitting end of the illumination-light deflecting portion, it is possible to deflect the illumination light by reflecting a large amount of the illumination light at the reflection surface facing the emitting end. By doing so, it is possible to reduce the illumination-light component incident on the emission surface without going via the reflection surface, and thus, it is possible to achieve highly efficient illumination by reducing the amount of return light and unwanted light.

In the above-described aspect, the illumination-light guiding portion and the illumination-light deflecting portion may be formed of separate members.

By employing such a configuration, it is possible to separately manufacture the illumination-light guiding portion and the illumination-light deflecting portion, thus enhancing the ease of manufacturing thereof.

In the above-described aspect, the illumination-light guiding portion and the illumination-light deflecting portion may be formed of an integrally formed single prism.

By doing so, it is possible to reduce the number of components, and thus, it is possible to enhance the illumination efficiency by reducing the Fresnel loss at the interface between the illumination-light guiding portion and the illumination-light deflecting portion.

In the above-described aspect, the illumination-light guiding portion and the illumination-light deflecting portion may be formed of separate prisms.

By doing so, it is possible to separately manufacture the illumination-light guiding portion and the illumination-light deflecting portion, thus enhancing the ease of manufacturing thereof.

In the above-described aspect, a step portion may be provided between the illumination-light guiding portion and the emission surface.

By doing so, of the illumination light emitted from the illumination-light guiding portion, the component incident on the emission surface without going via the reflection surface is reduced, and thus, it is possible to enhance the illumination efficiency by reducing the amount of return light and unwanted light.

Another aspect of the present invention is an image-acquisition apparatus comprising: an image-capturing optical system that has an optical axis and that captures an image of an area surrounding the optical axis; and a single or a plurality of the aforementioned illumination optical systems, disposed so as to surround the optical axis.

With this aspect, it is possible to capture, by using the image-capturing optical system, light coming from an observation subject illuminated at a high illumination efficiency over a large area by using one of the above-described illumination optical systems.

In the above-described aspect, the illumination-light guiding portion may guide the illumination light in a direction along the optical axis, a pair of the total reflection surfaces may be disposed closer to the optical axis than the emission surface is, and the illumination-light deflecting portion may deflect the illumination light both forward and rearward with respect to a plane that is perpendicular to the optical axis.

By doing so, of the illumination light emitted from the illumination-light guiding portion, the component incident on the emission surface without going via the reflection surface is reduced, and thus, it is possible to enhance the illumination efficiency by reducing the amount of return light and unwanted light.

In the above-described aspect, the emission surface may have a region that is inclined forward in a direction in which the emission surface approaches the optical axis, and the reflection surface may have a region that is inclined forward in a direction in which the reflection surface is separated from the optical axis.

By doing so, it is possible to tilt the illumination light emitted from the emission surface forward by means of the region that is inclined forward in the direction in which the emission surface approaches the optical axis, and it is possible to deflect the illumination light in a lateral direction and rearward by means of the region that is inclined forward with respect to the reflection surface in a direction in which the reflection surface becomes more distant from the optical axis.

In the above-described aspect, an absorbing member that absorbs unwanted light emitted from the emission surface may be provided further forward than the emission surface is.

By doing so, the absorbing member absorbs unwanted light in the illumination light emitted from the emission surface, and thus, it is possible to prevent the unwanted light from directly being made incident on an objective lens of the image-capturing optical system.

The present invention affords an advantage in that it is possible to enhance the use efficiency of illumination light, while allowing uniform illumination of a large area.

REFERENCE SIGNS LIST 1 endoscope (image-acquisition apparatus)
14 image-capturing optical system
15 illumination optical system
17 light guide
20 light source apparatus (light source portion)
23 illumination-light guiding portion
23a total reflection surface
24 illumination-light deflecting portion
24a emission surface
24b reflection surface
25 prism (illumination-light guiding portion, illumination-light deflecting portion)
29 illumination-light absorbing portion (absorbing member)
O optical axis

The invention claimed is:

1. An illumination optical system comprising:
an illumination-light guiding portion configured to guide illumination light emitted from a light source portion; and
an illumination-light deflecting portion configured to emit the illumination light guided thereto by the illumination-light guiding portion after deflecting the illumination light by means of reflection;
wherein, in one cross-section along a direction in which the illumination light travels,
the illumination-light guiding portion has a pair of total reflection surfaces in which the distance therebetween gradually increases in a forward traveling direction of the illumination light, and
the illumination-light deflecting portion is provided with (i) an emission surface from which the illumination light guided by the illumination-light guiding portion is emitted, and (ii) a reflection surface that has a convex shape facing the emission surface and that reflects the illumination light guided by the illumination-light guiding portion toward the emission surface.

2. The illumination optical system according to claim 1, wherein the illumination-light guiding portion has an emitting end from which the guided illumination light is emitted, and the reflection surface is disposed at a position facing the emitting end.

3. The illumination optical system according to claim 1, wherein the illumination-light guiding portion and the illumination-light deflecting portion are formed of separate members.

4. The illumination optical system according to claim 1, wherein the illumination-light guiding portion and the illumination-light deflecting portion are formed of an integrally formed single prism.

5. The illumination optical system according to claim 3, wherein the illumination-light guiding portion and the illumination-light deflecting portion are formed of separate prisms.

6. The illumination optical system according to claim 1, wherein a step portion is provided between the illumination-light guiding portion and the emission surface.

7. The illumination optical system according to claim 1, wherein a lateral cross-sectional shape of the illumination-light deflecting portion is a shape in which a portion of a ring is cut out in a radial direction, and a lateral cross-sectional shape of the illumination-light guiding portion is a ring shape or a shape in which a portion of a ring is cut out in a radial direction.

8. The illumination optical system according to claim 1, wherein a lateral cross-sectional shape of the illumination-light deflecting portion is a shape in which a portion of a ring is cut out in a radial direction, and the illumination-light guiding portion is provided with a plurality of arc-shaped light guiding portions that are disposed, in a circumferential direction with spaces therebetween, on a circumference about an axis along a direction in which the illumination light travels.

9. An image-acquisition apparatus comprising:
an image-capturing optical system that has an optical axis and that captures an image of an area surrounding the optical axis; and
a single or a plurality of illumination optical systems according to claim 1, disposed so as to surround the optical axis.

10. The image-acquisition apparatus according to claim 9, wherein:
the illumination-light guiding portion guides the illumination light in a direction along the optical axis,
a pair of the total reflection surfaces are disposed closer to the optical axis than the emission surface is, and
the illumination-light deflecting portion deflects the illumination light both forward and rearward with respect to a plane that is perpendicular to the optical axis.

11. The image-acquisition apparatus according to claim 10, wherein:
the emission surface has a region that is inclined forward in a direction in which the emission surface approaches the optical axis, and
the reflection surface has a region that is inclined forward in a direction in which the reflection surface is separated from the optical axis.

12. The image-acquisition apparatus according to claim 11, wherein an absorbing member that absorbs unnecessary light emitted from the emission surface is provided further forward than the emission surface is.

* * * * *